(12) United States Patent
Flohr et al.

(10) Patent No.: US 9,888,890 B2
(45) Date of Patent: Feb. 13, 2018

(54) FILTER ARRANGEMENT FOR CT SYSTEM HAVING A PLURALITY OF X-RAY SOURCES

(71) Applicant: Siemens Aktiengesellschaft, Munich (DE)

(72) Inventors: Thomas Flohr, Uehlfeld (DE); Bernhard Schmidt, Fuerth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 15/077,939

(22) Filed: Mar. 23, 2016

(65) Prior Publication Data
US 2016/0296183 A1    Oct. 13, 2016

(30) Foreign Application Priority Data
Apr. 9, 2015   (DE) .......................... 10 2015 206 363

(51) Int. Cl.
| G06K 9/00 | (2006.01) |
| A61B 6/00 | (2006.01) |
| A61B 6/03 | (2006.01) |
| G06T 11/00 | (2006.01) |

(52) U.S. Cl.
CPC ............ *A61B 6/4035* (2013.01); *A61B 6/032* (2013.01); *A61B 6/4014* (2013.01); *A61B 6/4078* (2013.01); *A61B 6/482* (2013.01); *A61B 6/5211* (2013.01); *G06T 11/005* (2013.01)

(58) Field of Classification Search
None
See application file for complete search history.

(56) References Cited

FOREIGN PATENT DOCUMENTS

| DE | 102007044549 | * | 4/2009 | ............... A61B 6/06 |
| DE | 102007044549 A1 | | 4/2009 | |
| DE | 202014002844 U1 | | 5/2014 | |
| EP | 2873967 A1 | | 5/2015 | |

OTHER PUBLICATIONS

German Office Action dated Nov. 26, 2015.

* cited by examiner

*Primary Examiner* — Fred Hu
(74) *Attorney, Agent, or Firm* — Harness, Dickey & Pierce, P.L.C.

(57) ABSTRACT

A filter arrangement is described. The filter arrangement includes an inner filter region, covering a cross-sectional area of a fan beam of a first X-ray source, and an outer filter region covering, together with the inner filter region, a larger cross-sectional area of a larger fan beam of a second X-ray source. The inner filter region has a first spectral filter function. The outer filter region is divided into a first subregion having a second spectral filter function and a second subregion having a third different spectral filter function. A computed tomography system is described. A method for producing a filter arrangement for a spectral filtering of X-ray radiation of a CT system having a first X-ray source and a second X-ray source is also presented. A method for reconstructing image data on the basis of projection measurement data is also described.

28 Claims, 4 Drawing Sheets

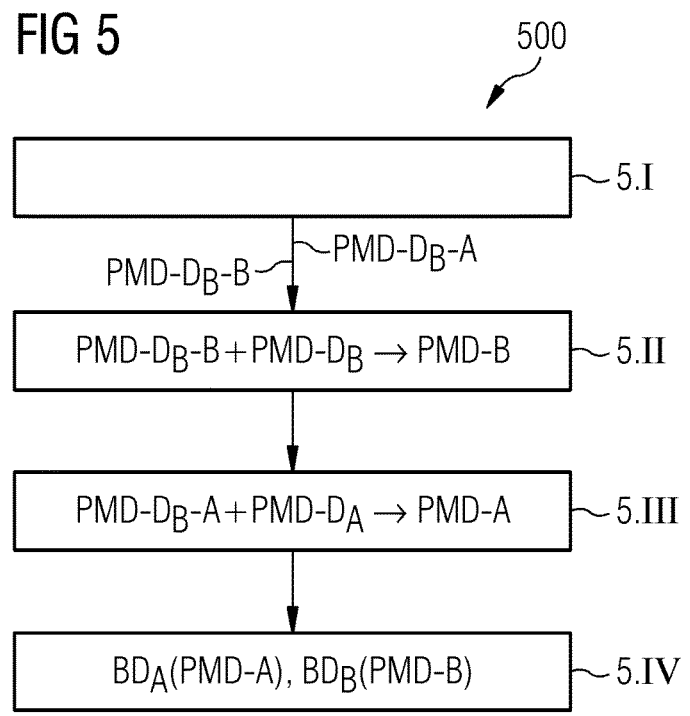

FILTER ARRANGEMENT FOR CT SYSTEM HAVING A PLURALITY OF X-RAY SOURCES

PRIORITY STATEMENT

The present application hereby claims priority under 35 U.S.C. § 119 to German patent application number DE 102015206363.1 filed Apr. 9, 2015, the entire contents of which are hereby incorporated herein by reference.

FIELD

At least one embodiment of the invention generally relates to a filter arrangement for a spectral filtering of X-ray radiation of a computed tomography system having a first and a second X-ray source. At least one embodiment of the invention furthermore generally relates to a computed tomography system having a first X-ray source with a first X-ray energy level, which emits a first fan beam with a first fan-beam arc, having a second X-ray source with a second X-ray energy level, which emits a second fan beam with a second fan-beam arc where the second fan-beam arc is larger than the first fan-beam arc, and having a first X-ray detector which is set up in order to detect the first fan beam emitted by the first X-ray source, and having a second X-ray detector which is set up in order to detect the second fan beam emitted by the second X-ray source. At least one embodiment of the invention moreover generally relates to a method for producing a filter arrangement for a spectral filtering of the X-ray radiation from an X-ray source of a CT system. In addition at least one embodiment of the invention generally relates to a method for reconstructing image data on the basis of projection measurement data which has been acquired via a computed tomography system.

BACKGROUND

In contrast to conventional single-tube CT systems, a dual-source computed tomography system (CT system) has two X-ray tubes arranged at an angle of approximately 90 degrees relative to each other, each with a detector system located opposite. The two tubes can be operated at different energy levels, which results in a differentiated energy spectrum of tissues having a similar density. It thereby becomes possible to distinguish structures having different tissue from one another (for example bones and vessels filled with contrast agent) and also to quantitatively evaluate the structures. The dual-source technology enables a direct subtraction of vessels and bones during the image capture operation, a tumor characterization and a differentiation of fluids.

Normally, with dual-source CT devices tube-side prefilters are installed in order to increase the spectral separation. In other words the energy spectra which already differ on account of the different X-ray tubes are further differentiated with the aid of a prefilter. Conventionally, 0.4 mm to 0.6 mm thick tin prefilters are used which are introduced on the tube side into the beam path of the X-ray tube which is operated at the higher electrical voltage, for example 140 kV or 150 kV. The mean energy level of the spectrum of the X-rays is thereby shifted towards higher values, which means that the spectral separation of the X-ray radiation, with which different structures that consist of different materials are made visible, is improved.

However, the problem exists with regard to conventional systems that on account of spatial restrictions in the CT gantry only one detector is able to cover the full measuring field having a 50 cm diameter but the other detector is restricted to a smaller measuring field. The smaller measuring field normally encompasses a region having a diameter of only 26 to 35 cm. Outside the small measuring field therefore no data is available for both X-ray spectra in the case of conventional dual-source CT devices, which means that only the inner region, in other words the smaller measuring field, is scanned with both X-ray spectra. There are however applications, such as for example the acquisition of data for calculating electron density distributions in radiotherapy, in which data from the entire patient must be available, in other words in the entire measuring field.

SUMMARY

At least one embodiment of the present invention enables an image capture operation of large-size objects or object sections with the aid of a CT system using X-rays having at least two different energy spectra.

At least one embodiment is directed to a filter arrangement; at least one embodiment is directed to a computed tomography system; at least one embodiment is directed to a method for producing a filter arrangement; and at least one embodiment is directed to a method for reconstructing image data on the basis of projection measurement data.

The filter arrangement according to at least one embodiment of the invention for a spectral filtering of the X-ray radiation of a CT system having a first and a second X-ray source has an inner filter region which covers a cross-sectional area of a fan beam of the second X-ray source with a second, larger fan-beam arc, where the partial cross-sectional area is chosen in accordance with a first, smaller fan-beam arc of a fan beam of the first X-ray source. The fan beam of the first X-ray source is acquired by a smaller detector, the dimensions of which correspond to those of the fan beam of the first X-ray source.

In addition, the filter arrangement according to at least one embodiment of the invention has an outer filter region which together with the inner filter region covers a cross-sectional area of the fan beam of the second X-ray source which is larger in relation to the inner partial cross-sectional area. The two measuring fields covered by the differently dimensioned fan beams are, as already mentioned, of different sizes in the case of CT systems having a plurality of X-ray sources. The inner filter region corresponding in terms of the dimensions to the smaller measuring field has a first spectral filter function.

It should be noted here that the filter arrangement is provided in order to be inserted into the beam path of the larger fan beam to which a larger detector is assigned, the dimensions of which correspond to the larger measuring field. On the other hand, the filter arrangement according to at least one embodiment of the invention has a conventional filter function in the inner filter region, where the mean energy of the spectrum of the X-ray radiation in the small measuring field is increased.

The computed tomography system according to at least one embodiment of the invention has a first X-ray source with a first X-ray energy level, which emits a first fan beam with a first fan-beam arc. In addition the computed tomography system according to at least one embodiment of the invention has a second X-ray source with a second X-ray energy level, which emits a second fan beam with a second fan-beam arc, where the second fan-beam arc is larger than the first fan-beam arc. Due to design considerations the second fan beam therefore covers a larger measuring field than the first fan beam. The computed tomography system according to at least one embodiment of the invention comprises a first X-ray detector, corresponding to the first X-ray source, which is set up in order to detect the first fan beam emitted by the first X-ray source, and a second X-ray detector, corresponding to the second X-ray source, which is set up in order to detect the second fan beam emitted by the second X-ray source. The computed tomography system according to at least one embodiment of the invention moreover has the filter arrangement according to at least one embodiment of the invention.

With regard to the method according to at least one embodiment of the invention for producing a filter arrangement for a spectral filtering of X-ray radiation of a CT system having a first X-ray source and a second X-ray source, an inner filter region is formed which covers an inner partial cross-sectional area of a fan beam of the second X-ray source with a second, larger fan-beam arc, where the partial cross-sectional area is chosen in accordance with a first, smaller fan-beam arc of a fan beam of the first X-ray source, and has a first spectral filter function. Furthermore, an outer filter region is formed which together with the inner filter region covers a cross-sectional area of the fan beam of the second X-ray source which is larger in relation to the inner partial cross-sectional area. In addition, the outer filter region is divided into two subregions in the z direction, in other words in the direction of the system axis, where the first subregion is designed with a second spectral filter function and the second subregion has been designed with a third spectral filter function different from the second spectral filter function.

With regard to the method according to at least one embodiment of the invention for reconstructing image data on the basis of projection measurement data which has been acquired via the computed tomography system according to at least one embodiment of the invention, the projection measurement data from the outer detector regions of the second detector is initially separated depending on whether the projection measurement data is assigned to the first subregion of the outer filter region of the filter arrangement or whether the projection measurement data is assigned to the second subregion of the outer filter region of the filter arrangement.

Furthermore, the separated projection measurement data of the first subregion of the outer filter region of the filter arrangement is assigned to the projection measurement data of the second X-ray detector such that a first projection measurement data set is formed on the basis of the acquired X-ray radiation of the first X-ray spectrum. Accordingly, the separated projection measurement data of the second subregion of the outer filter region of the filter arrangement is assigned to the projection measurement data of the first X-ray detector such that a second projection data set is formed on the basis of acquired X-ray radiation having a second X-ray spectrum. Prior to the reconstruction of image data on the basis of the acquired raw data, in other words the projection measurement data, a division of the projection measurement data therefore takes place according to the energy spectrum of the X-ray radiation, the detection of which resulted in generation of the respective projection measurement data. Finally, image data is reconstructed separately on the basis of the first projection data set and the second projection measurement data set. Images of different structures can subsequently be produced by addition and/or subtraction, possibly also weighted, of the separately reconstructed image data.

The method according to at least one embodiment of the invention for reconstructing image data on the basis of projection measurement data which has been acquired via a computed tomography system according to at least one embodiment of the invention can also be implemented in the form of a computer program. A largely software-based implementation has the advantage that reconstruction facilities already used previously can also be upgraded in a simple manner via a software update in order to operate in the inventive manner. In this respect, at least one embodiment is directed to a computer program product or medium which can be loaded directly into a memory facility of a computed tomography system, having program sections in order to execute all the steps for reconstructing image data on the basis of projection measurement data which has been acquired via a computed tomography system acquired according to at least one embodiment of the invention when the program is executed in the memory facility.

The dependent claims and also the following description in each case contain particularly advantageous embodiments and developments of the invention. In this situation the claims in a claim category can in particular also be developed analogously to the dependent claims in a different claim category. In addition, the different features of various example embodiments and claims can also be combined in the context of the invention to produce new example embodiments.

BRIEF DESCRIPTION OF THE DRAWINGS

The invention will be described again in detail in the following with reference to the attached figures on the basis of example embodiments. In the drawings:

FIG. 5 shows a flowchart which illustrates a method for reconstructing image data on the basis of projection measurement data which has been acquired via a computed tomography system in accordance with an example embodiment of the invention.

DETAILED DESCRIPTION OF THE EXAMPLE EMBODIMENTS

Figure 1:
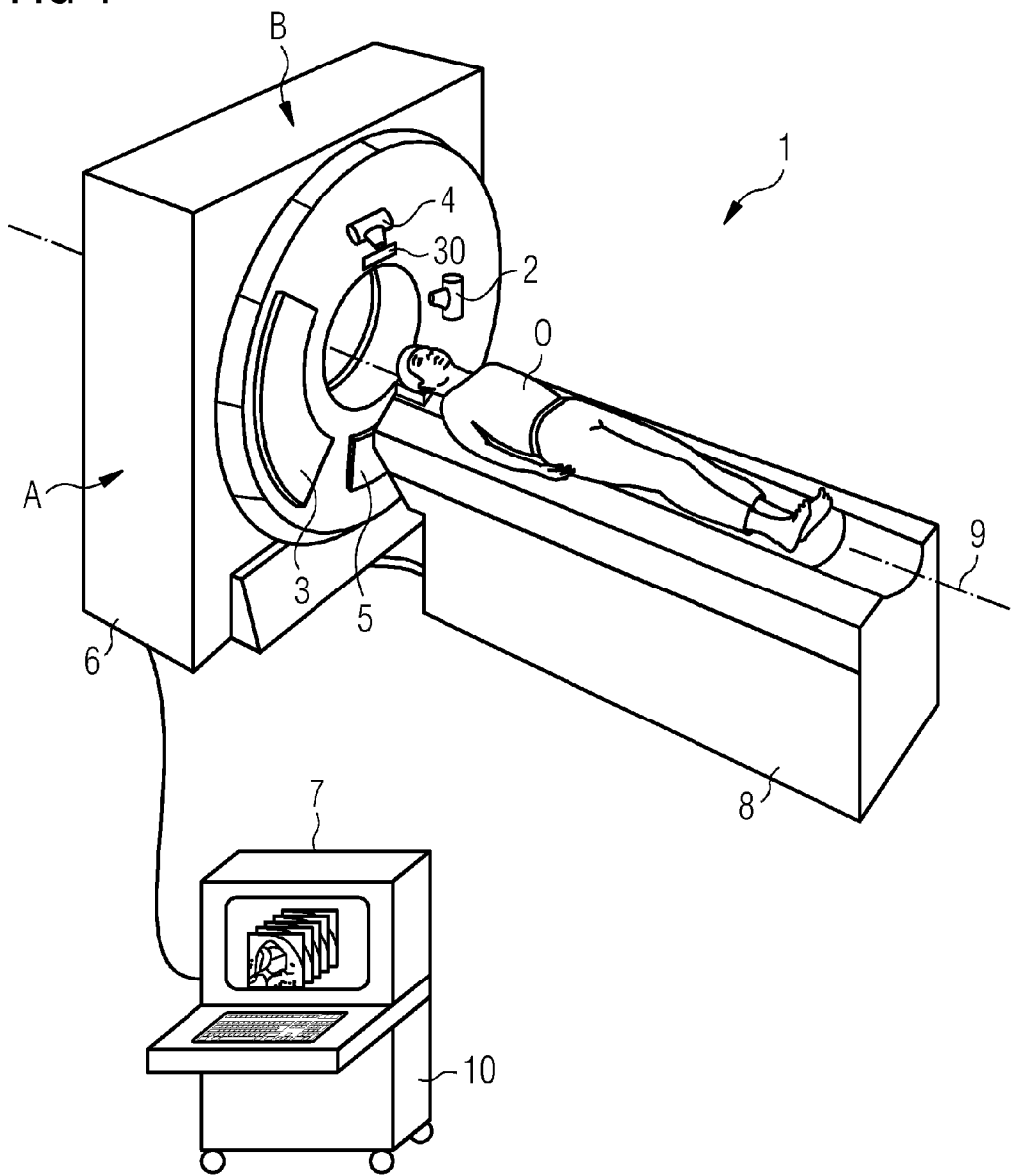
FIG. 1 shows a schematic illustration of an X-ray computed tomography system having a filter arrangement in accordance with an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

The filter arrangement according to at least one embodiment of the invention for a spectral filtering of the X-ray radiation of a CT system having a first and a second X-ray source has an inner filter region which covers a cross-sectional area of a fan beam of the second X-ray source with a second, larger fan-beam arc, where the partial cross-sectional area is chosen in accordance with a first, smaller fan-beam arc of a fan beam of the first X-ray source. The fan beam of the first X-ray source is acquired by a smaller detector, the dimensions of which correspond to those of the fan beam of the first X-ray source.

In addition, the filter arrangement according to at least one embodiment of the invention has an outer filter region which together with the inner filter region covers a cross-sectional area of the fan beam of the second X-ray source which is larger in relation to the inner partial cross-sectional area. The two measuring fields covered by the differently dimensioned fan beams are, as already mentioned, of different sizes in the case of CT systems having a plurality of X-ray sources. The inner filter region corresponding in terms of the dimensions to the smaller measuring field has a first spectral filter function.

It should be noted here that the filter arrangement is provided in order to be inserted into the beam path of the larger fan beam to which a larger detector is assigned, the dimensions of which correspond to the larger measuring field. On the other hand, the filter arrangement according to at least one embodiment of the invention has a conventional filter function in the inner filter region, where the mean energy of the spectrum of the X-ray radiation in the small measuring field is increased.

According to at least one embodiment of the invention, the outer filter region of the filter arrangement is moreover divided into two subregions in the z direction, in other words in the direction of the system axis, which corresponds to the axis of rotation of the CT system, where the first subregion has a second spectral filter function and the second subregion has a third spectral filter function different from the second filter function. In the fan-beam direction, in other words when viewed in the circumferential direction of the CT system in the outer region, the filter surface areas are divided into two subregions in the z direction, in other words in the axial direction of the CT system, which have a differing effect on the incident X-ray radiation, such that even if X-ray radiation of the same spectrum falls onto both subregions the X-ray radiation emanating from the two filter subregions has a different energy spectrum. Although different regions of the measuring field are initially also irradiated by the X-ray radiation from the two filter subregions, a complete scanning of the measuring field with X-ray radiation from the two filter subregions is however achieved via rotation of the gantry and a simultaneous linear movement of the patient table. The projection measurement data generated from the detected X-ray radiation for X-ray radiation with different energy spectra can then be used in order to reconstruct images of different structures consisting of different substances.

The filter arrangement according to at least one embodiment of the invention has the advantage which cannot be emphasized enough that the structure of a conventional CT system having a plurality of X-ray sources with different X-ray spectra can be adopted and in order to achieve the aforementioned object only one conventional filter needs to be replaced by the filter arrangement according to the invention as far as the hardware of the system is concerned. A highly effective and at the same time cost-effective solution to the problem described above has thus been found.

The computed tomography system according to at least one embodiment of the invention has a first X-ray source with a first X-ray energy level, which emits a first fan beam with a first fan-beam arc. In addition the computed tomography system according to at least one embodiment of the invention has a second X-ray source with a second X-ray energy level, which emits a second fan beam with a second fan-beam arc, where the second fan-beam arc is larger than the first fan-beam arc. Due to design considerations the second fan beam therefore covers a larger measuring field than the first fan beam. The computed tomography system according to at least one embodiment of the invention comprises a first X-ray detector, corresponding to the first X-ray source, which is set up in order to detect the first fan beam emitted by the first X-ray source, and a second X-ray detector, corresponding to the second X-ray source, which is set up in order to detect the second fan beam emitted by the second X-ray source. The computed tomography system according to at least one embodiment of the invention moreover has the filter arrangement according to at least one embodiment of the invention.

With regard to the method according to at least one embodiment of the invention for producing a filter arrangement for a spectral filtering of X-ray radiation of a CT system having a first X-ray source and a second X-ray source, an inner filter region is formed which covers an inner partial cross-sectional area of a fan beam of the second X-ray source with a second, larger fan-beam arc, where the partial cross-sectional area is chosen in accordance with a first, smaller fan-beam arc of a fan beam of the first X-ray source, and has a first spectral filter function. Furthermore, an outer filter region is formed which together with the inner filter region covers a cross-sectional area of the fan beam of the second X-ray source which is larger in relation to the inner partial cross-sectional area. In addition, the outer filter region is divided into two subregions in the z direction, in other words in the direction of the system axis, where the first subregion is designed with a second spectral filter function and the second subregion has been designed with a third spectral filter function different from the second spectral filter function.

With regard to the method according to at least one embodiment of the invention for reconstructing image data on the basis of projection measurement data which has been acquired via the computed tomography system according to at least one embodiment of the invention, the projection measurement data from the outer detector regions of the second detector is initially separated depending on whether the projection measurement data is assigned to the first subregion of the outer filter region of the filter arrangement or whether the projection measurement data is assigned to the second subregion of the outer filter region of the filter arrangement.

Furthermore, the separated projection measurement data of the first subregion of the outer filter region of the filter arrangement is assigned to the projection measurement data of the second X-ray detector such that a first projection measurement data set is formed on the basis of the acquired X-ray radiation of the first X-ray spectrum. Accordingly, the separated projection measurement data of the second subregion of the outer filter region of the filter arrangement is assigned to the projection measurement data of the first X-ray detector such that a second projection data set is formed on the basis of acquired X-ray radiation having a second X-ray spectrum. Prior to the reconstruction of image data on the basis of the acquired raw data, in other words the projection measurement data, a division of the projection measurement data therefore takes place according to the energy spectrum of the X-ray radiation, the detection of which resulted in generation of the respective projection measurement data. Finally, image data is reconstructed separately on the basis of the first projection data set and the second projection measurement data set. Images of different structures can subsequently be produced by addition and/or subtraction, possibly also weighted, of the separately reconstructed image data.

The method according to at least one embodiment of the invention for reconstructing image data on the basis of projection measurement data which has been acquired via a computed tomography system according to at least one embodiment of the invention can also be implemented in the form of a computer program. A largely software-based implementation has the advantage that reconstruction facilities already used previously can also be upgraded in a simple manner via a software update in order to operate in the inventive manner. In this respect, at least one embodiment is directed to a computer program product or medium which can be loaded directly into a memory facility of a computed tomography system, having program sections in order to execute all the steps for reconstructing image data on the basis of projection measurement data which has been acquired via a computed tomography system acquired according to at least one embodiment of the invention when the program is executed in the memory facility.

The dependent claims and also the following description in each case contain particularly advantageous embodiments and developments of the invention. In this situation the claims in a claim category can in particular also be developed analogously to the dependent claims in a different claim category. In addition, the different features of various example embodiments and claims can also be combined in the context of the invention to produce new example embodiments.

The filter arrangement according to at least one embodiment of the invention is preferably embodied as a prefilter arrangement. In this variant the filter is arranged on the tube side, in other words between X-ray source and object to be imaged. Such an arrangement of the filter has the advantage that part of the X-ray radiation emitted by the X-ray source is absorbed by the filter which means that the dose to the object under examination, for example a patient, is reduced.

Alternatively the filter arrangement can also be embodied as a postfilter arrangement. In this variant the filter is arranged on the detector side, in other words between detector and object to be imaged. Such an arrangement of the filter does however have the result that the X-ray radiation emitted by the X-ray source strikes the object to be imaged unfiltered, which means that dose to the object to be imaged, for example a patient or a subregion of a patient, is relatively high.

By preference, the filter arrangement is embodied in such a manner that the inner filter region is designed as a single piece. In this variant the inner filter region corresponds to a conventional filter of a CT system having a plurality of X-ray sources with different X-ray spectra. On the other hand the outer sections of the filter according to the invention are however constructed in the manner described above such that unlike in the case of a conventional arrangement projection measurement data for different X-ray spectra can also be captured in the outer region of the measuring field.

In a likewise preferred variant of the filter arrangement according to at least one embodiment of the invention the inner filter region comprises a first filter material which covers the entire width of a detector of the CT system in the direction of the system axis or in the z direction. The detector is the detector which detects the X-ray radiation from the second X-ray source.

The first filter material may for example comprise tin. Tin is suitable for shifting the spectrum of X-ray radiation towards higher energy levels. Should an improved spectral separation of the acquired projection measurement data which has been generated using X-ray radiation from different X-ray sources be desired, then it is advantageous if the energy spectrum of the X-ray radiation is shifted towards an energy spectrum with a higher energy level. Tin is particularly well suited for such a spectral shift.

In a very effective embodiment of the filter arrangement according to at least one embodiment of the invention the outer filter region comprises a second filter material and a third filter material different from the second filter material. By using different filter materials for the two subregions of the outer filter region, a differing spectral filter function is also achieved for the different subregions which means that the outer measuring field is also irradiated with X-ray radiation having different spectra and consequently projection measurement data can be generated for this region on the basis of X-ray radiation having a differing spectral structure. Structures consisting of different substances can thereby also be imaged separately from one another in the outer measuring field.

In a particularly practicable variant the first filter material and the second filter material are identical.

For example, the second filter material can comprise tin and the third filter material can comprise gold.

Alternatively or in combination with the previous embodiments of the filter arrangement according to at least one embodiment of the invention the first subregion and the second subregion of the outer filter region can have differing thicknesses or differing densities. Filters having differing material thicknesses or differing densities can also be used to effect shifts of X-ray spectra towards different energy levels. This type of dimensioning of the filters can also be combined with the choice of the filter material.

In a particularly advantageous embodiment of the filter arrangement according to at least one embodiment of the invention the first subregion and the second subregion of the outer filter region each occupy half of the outer filter region. With this design of the subregions of the outer filter region a uniformly distributed capture of raw data using X-ray radiation from both subregions can be easily implemented.

Such a uniform division of the two subregions can for example be realized in that the two subregions are designed in such a manner that the first subregion and the second subregion of the outer filter region meet in the center of the outer filter region when viewed in the z direction.

In a variant of the computed tomography system according to at least one embodiment of the invention the first X-ray detector has a smaller extent in the fan-beam direction than the second X-ray detector. The differing dimensioning of two X-ray detectors can result for example from structural design considerations due to the ring shape of the gantry of the CT system and also the arrangement of the X-ray detectors. Particularly in such cases where the dimensioning of the detectors is restricted by structural design considerations the filter arrangement according to at least one embodiment of the invention proves to be particularly advantageous because images can also be captured in this case in the outer measuring field using X-rays having different energy spectra. The fan-beam direction is to be understood as the direction which the fan-beam arc of the respective fan beam spans. This direction also corresponds to the direction of rotation of X-ray source and detector. It normally runs orthogonal to the system axis and to the direction of propagation of the X-ray radiation.

In a preferred embodiment of the computed tomography system according to at least one embodiment of the invention, when viewed in the fan-beam direction the second X-ray detector has outer detector regions which correspond to the outer filter regions of the filter arrangement and are set up in order to detect X-rays having a differing energy level which have been generated as a result of a differential X-ray beam hardening by the differing spectral filter functions of the first subregion and of the second subregion of the outer filter region. It is for example possible to parameterize different detector regions differently in order to adapt them to different energy levels.

By particular preference the computed tomography system according to at least one embodiment of the invention has a reconstruction facility which is set up in order to use the X-ray radiation acquired in the outer detector regions using differing energy levels for dual-energy imaging.

Particularly precise imaging is achieved if the computed tomography system according to at least one embodiment of the invention is set up in order to perform an image capture operation using a pitch of a spiral scan of less than 0.75. In the case of dual-energy systems having two X-ray sources of conventional construction the pitch of the spiral scan is normally restricted to 1.5. Since, according to at least one embodiment of the invention, the detector surface in the z direction is divided into two subregions for two different spectra, a maximum pitch of 0.75 results for the imaging facility according to at least one embodiment of the invention.

The X-ray system (1) shown in FIG. 1 is an X-ray computed tomography system 1. This has a gantry housed in a gantry housing 6, on which gantry are mounted two radiation source/detector systems A, B in angular offset fashion which are in each case formed by an X-ray tube 2, 4 and a detector 3, 5 located opposite. An object under examination O, here a patient, is situated on a patient table 8 which can be moved along a system axis 9 and can during the examination be slid in this manner through a measuring field in the region of the radiation source/detector systems A, B. The X-ray computed tomography system 1 can be controlled and where applicable also the image processing can be performed via a normal control unit 7. The control unit 7 has for example an image reconstruction facility 10. A filter arrangement 30 in accordance with an example embodiment of the invention is also drawn in FIG. 1. This is situated in the beam path of the second X-ray tube 4 and is embodied in this special example embodiment as a prefilter, in other words the filter arrangement 30 is positioned as a prefilter between the X-ray tube 4 and the object O to be imaged.

Figure 2:
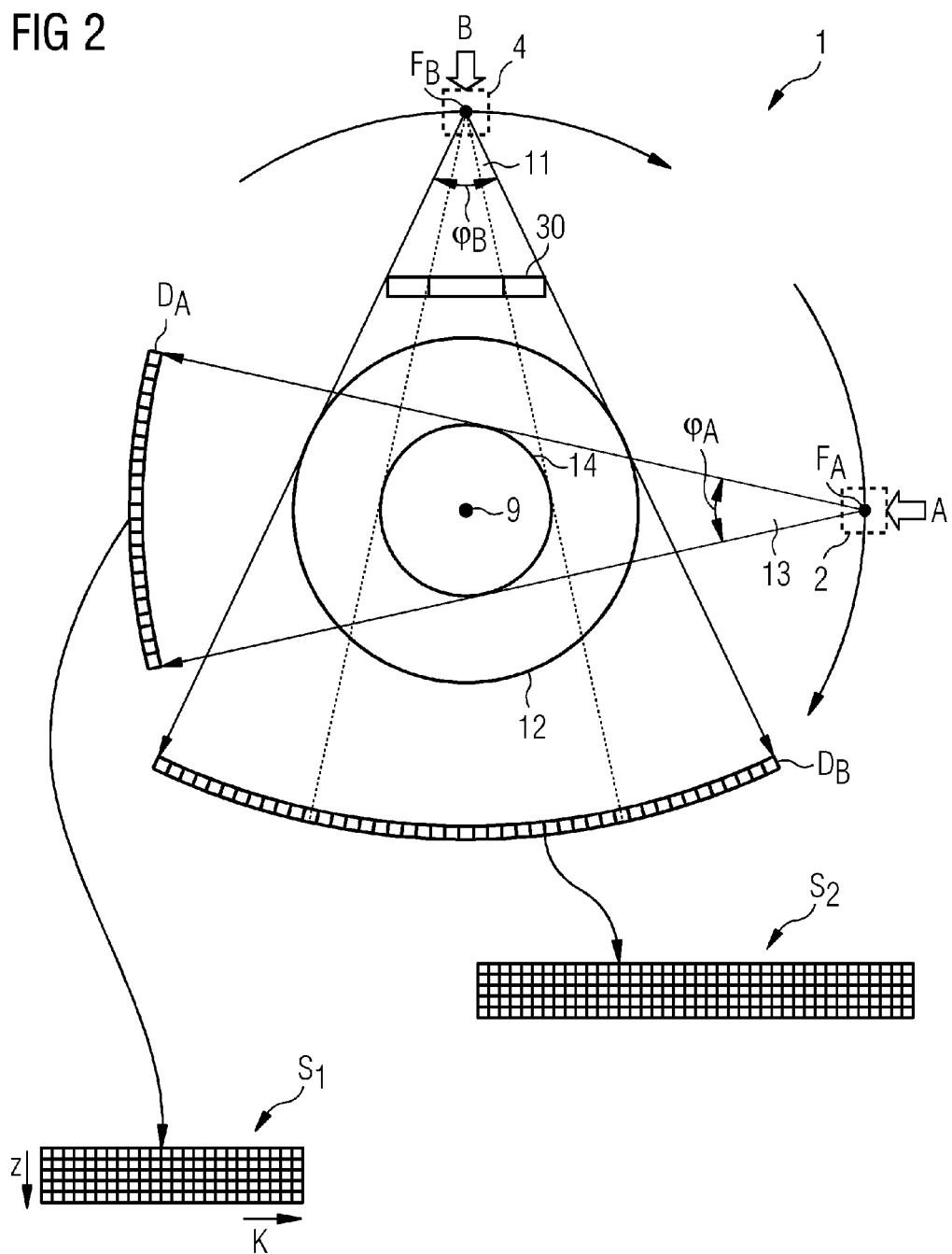
FIG. 2 shows a schematic illustration of a section through an X-ray computed tomography system having two X-ray sources and detector systems and also a filter arrangement in accordance with an example embodiment of the invention.

FIG. 2 shows the X-ray computed tomography system 1 in section perpendicular to the system axis 9. Illustrated is the first radiation source/detector system A having the X-ray tube 2, with the focus FA contained therein and with the detector plane DA from the detector system 3 situated opposite. The ray cone or fan beam 13 of the radiation source/detector system A has a fan-beam arc $\varphi A$ which, relative to the ray cone or fan beam 11 angularly offset by 90° of the likewise illustrated second radiation source/detector system B, satisfies the condition $\varphi a < \varphi b$. The second radiation source/detector system B consists of the X-ray tubes 4 with the focus FB and the detector plane DB situated opposite.

Illustrated schematically beneath the radiation source/detector systems A, B are the structures of two projection data sets S1, S2, the first projection data set S1 of which has been obtained during a measurement with the first radiation source/detector system A and the second projection data set S2 has been obtained at the same time with the second radiation source/detector system B.

With regard to the illustrated structure of the projection data sets S1, S2, a channel index K runs from left to right while a row index Z runs from bottom to top, where the row index Z therefore indicates the progress of the examination through movement of the object under examination E along the system axis 9 while the channel index K corresponds to the respective angles $\varphi A$, $\varphi B$.

With regard to the acquisition of projection data, also referred to as projection measurement data in the following, the X-ray tubes 2, 4 of the radiation source/detector systems A, B are operated with differing X-ray voltages, for example the X-ray tube 2 of the first system A at 80 kV and the X-ray tube of the second system B at 140 kV. In other words, the two radiation source/detector systems A, B measure using different X-ray energy levels E1, E2. A low-energy projection data set and a high-energy projection data set are thus generated simultaneously during a measurement.

In the CT system 1 illustrated in FIG. 2 the two radiation source/detector systems A, B have different geometries which means that the scanned measurement regions 12, 14, represented by the concentric circles, of the two radiation source/detector systems A, B are of different sizes. For this reason, projection data for both energy levels is conventionally available only for the inner measurement region 14. In order to also obtain a low-energy projection data set and a high-energy projection data set for the larger measurement region 12 a filter 30, in this case a prefilter 30, is introduced into the beam path of the second system B in accordance with an example embodiment of the invention. The prefilter 30 is set up in order to modify in differential spectral fashion the X-ray radiation emitted by the X-ray tube 4 of the second system B in different filter regions such that X-ray radiation having a different spectrum is acquired in the outer regions of the detectors DB of the second system B and a low-energy projection data set and a high-energy projection data set can thus also be acquired from the larger measurement region 12.

Figure 3:
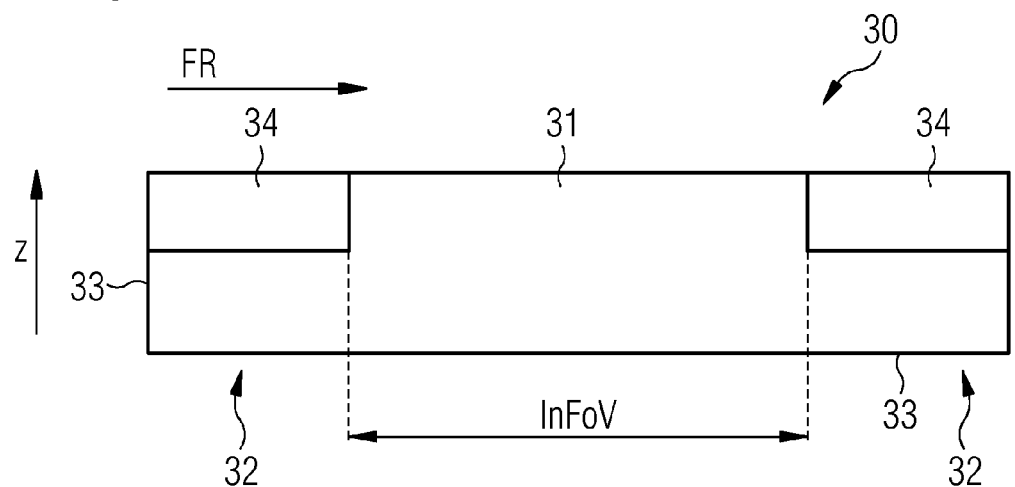
FIG. 3 shows a schematic illustration of a filter arrangement in accordance with an example embodiment of the invention.

FIG. 3 shows a schematic illustration of a filter 30 in accordance with an example embodiment of the invention. The filter 30 comprises an inner region 31 which exhibits a uniform filter effect and corresponds to the inner region of the detector DB of the second system B or to the Inner Field of View InFoV, which corresponds to the smaller or inner measurement region 14 in FIG. 2. In this region the filter 30 functions like a conventional filter which serves to increase the spectral separation of the X-ray radiation through this region of the filter in comparison with the X-ray radiation of the first system A by increasing the mean energy level of the X-ray radiation passing through the inner part 31 of the filter 30.

In order that X-ray radiation having two different energy levels is also present from the outer measurement region 12, the sections of the filter 30 to be designated as outer regions 32 of the filter 30 when viewed in the fan-beam direction FR are now divided into two different filter subregions 33, 34, where the first filter subregion 33 in the example embodiment shown has a filter effect which corresponds to the filter effect of the inner region 31, and the second filter subregion 34 has a filter effect which is different to the filter effect of the inner region 31. In other words, the spectrum of the X-ray radiation passing through the two outer filter subregions 33, 34 is modified differently. In this manner, X-ray radiation having a differing energy spectrum falls on different subregions 33, 34 of the outer regions 32 of the detector DB of the second system B, which means that X-ray radiation having two different energy levels is also detected from the outer measurement region 12 and low-energy projection data and high-energy projection data can therefore also be generated from this region 12 (see FIG. 2).

Figure 4:
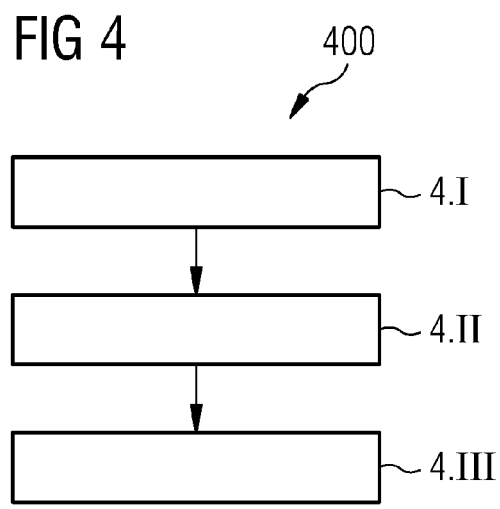
FIG. 4 shows a flowchart which illustrates a method for producing a filter arrangement in accordance with an example embodiment of the invention.

FIG. 4 shows a flowchart which illustrates a method 400 for producing a filter arrangement in accordance with an example embodiment of the invention. In the step 4.I an inner single-piece filter region is formed which covers a cross-sectional area of a fan beam of a first X-ray source and has a first spectral filter function. Subsequently in the step 4.II an outer filter region is formed which together with the inner filter region covers a larger cross-sectional area of a larger fan beam of a second X-ray source. Finally in the step 4.III the outer filter region 32 is divided into two subregions 33, 34 in the direction of the system axis, where the first subregion 33 is designed with a second spectral filter function and the second subregion 34 is designed with a third spectral filter function different from the second spectral filter function.

FIG. 5 shows a flowchart which illustrates a method 500 for reconstructing image data on the basis of projection measurement data which has been acquired via a computed tomography system in accordance with an example embodiment of the invention. With regard to the method 500, in the step 5.I projection measurement data PMD-DB-A, PMD-DB-B from the outer detector regions of the second detector DB, is separated depending on whether the projection measurement data PMD-DB-B is assigned to the first subregion 33 of the outer filter region 32 of the filter arrangement 30 or whether the projection measurement data PMD-DB-A is assigned to the second subregion 34 of the outer filter region 32 of the filter arrangement 30. In other words, a separation of the projection measurement data therefore takes place depending on which subregion of the outer detector region of the second X-ray detector DB the projection measurement data has been acquired in. In this situation a first subregion of the outer detector region of the second X-ray detector DB is assigned to the first subregion 33 of the outer filter region 32 of the filter arrangement 30 and a second subregion of the outer detector region of the second X-ray detector DB is assigned to the second subregion 34 of the outer filter region 32 of the filter arrangement 30.

In the step 5.II the separated projection measurement data PMD-DB-B of the first subregion 33 of the outer filter region 32 of the filter arrangement 30 is assigned to the projection measurement data PMD-DB of the second X-ray detector DB such that a first projection data set PMD-B is formed on the basis of acquired X-ray radiation using a first X-ray spectrum. In the step 5.III the separated projection measurement data PMD-DB-A of the second subregion 34 of the outer filter region 32 of the filter arrangement 30 is assigned to the projection measurement data PMD-DA of the first X-ray detector DA such that a second projection data set PMD-A is formed on the basis of acquired X-ray radiation using a second X-ray spectrum.

Finally in the step 5.IV image data BDA, BDB is reconstructed on the basis of the first projection measurement data set PMD-B and the second projection measurement data set PMD-A. In this situation the usual reconstruction methods can be employed, for example on the basis of a filtered backprojection. Different structures can be made visible with the aid of the two separately reconstructed image data sets. On the basis of the raw data, image data is calculated separately for differing energy levels. A spectral postprocessing can then take place on the basis of the image data and, for example, a bone structure can be depicted. As described above, images of different structures can be generated through addition and/or subtraction, possibly also weighted, of the separately reconstructed image data.

Finally, it should be noted once again that methods and devices described above are only preferred example embodiments of the invention and that the invention can be varied by the person skilled in the art without departing from the scope of the invention, insofar as it is predetermined by the claims. The filter arrangement and the computed tomography system have thus primarily been described on the basis of a computed tomography system having a fan-shaped X-ray form. The invention is however also applicable to other geometries of X-rays and detectors in which the surface area of the two detectors is dimensioned differently. A number of different X-ray spectra greater than two is also conceivable. It should also be noted for the sake of completeness that the use of the indefinite article "a" does not mean that the features in question cannot be present in a multiple manner.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. §112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A filter arrangement for a spectral filtering of X-ray radiation of a CT system including a first and a second X-ray source, comprising:
    an inner filter region, to cover an inner partial cross-sectional area of a fan beam of the second X-ray source with a second, relatively larger fan-beam arc, the inner partial cross-sectional area being chosen in accordance with first, relatively smaller fan-beam arc of a fan beam of the first X-ray source, the inner filter region including a first spectral filter function; and
    an outer filter region to, together with the inner filter region, cover a cross-sectional area of the fan beam of the second X-ray source, which is relatively larger in relation to the partial cross-sectional area, the outer filter region being divided into two subregions in a direction of the system axis of the CT system, the first subregion including a second spectral filter function and the second subregion including a third spectral filter function, different from the second filter function.

2. The filter arrangement of claim 1, wherein the filter arrangement is designed as a prefilter arrangement.

3. The filter arrangement of claim 1, wherein the inner filter region includes a first filter material to cover an entire width of a detector of the CT systems in a direction of the system axis.

4. The filter arrangement of claim 3, wherein the first filter material comprises tin.

5. The filter arrangement of claim 3, wherein the outer filter region includes a second filter material and a third filter material, different from the second filter material.

6. The filter arrangement of claim 5, wherein at least one of:
    the second filter material comprises tin, and
    the third filter material comprises gold.

7. The filter arrangement of claim 1, wherein at least one of
    the first subregion and the second subregion of the outer filter region include differing thicknesses or differing densities, and
    the first subregion and the second subregion of the outer filter region each occupy half of the outer filter region.

8. The filter arrangement of claim 1, wherein the first subregion and the second subregion of the outer filter region meet in a center of the outer filter region when viewed in a direction of the system axis.

9. A computed tomography system, comprising:
    a first X-ray source with a first X-ray energy level, to emit a first fan beam with a first fan-beam arc;
    a second X-ray source with a second X-ray energy level, to emit a second fan beam with a second fan-beam arc, the second fan-beam arc being relatively larger than the first fan-beam arc;
    a first X-ray detector, to detect the first fan beam emitted by the first X-ray source;
    a second X-ray detector, to detect the second fan beam emitted by the second X-ray source; and
    the filter arrangement of claim 1.

10. The computed tomography system of claim 9, wherein the first X-ray detector includes a relatively smaller extent in the fan-beam direction than the second X-ray detector.

11. The computed tomography system of claim 9, wherein the computed tomography system is set up to perform an image capture operation using a pitch of a spiral scan of less than 0.75.

12. The computed tomography system of claim 10, wherein the computed tomography system is set up to perform an image capture operation using a pitch of a spiral scan of less than 0.75.

13. The filter arrangement of claim 1, wherein the inner filter region is designed as a single piece.

14. The filter arrangement of claim 2, wherein the inner filter region is designed as a single piece.

15. The filter arrangement of claim 2, wherein the inner filter region includes a first filter material to cover an entire width of a detector of the CT systems in a direction of the system axis.

16. The filter arrangement of claim 15, wherein the first filter material comprises tin.

17. The filter arrangement of claim 3, wherein the first filter material and the second filter material are identical.

18. The filter arrangement of claim 5, wherein the first filter material and the second filter material are identical.

19. The filter arrangement of claim 18, wherein at least one of:
the second filter material comprises tin, and
the third filter material comprises gold.

20. A computed tomography system, comprising:
a first X-ray source with a first X-ray energy level, to emit a first fan beam with a first fan-beam arc;
a second X-ray source with a second X-ray energy level, to emit a second fan beam with a second fan-beam arc, the second fan-beam arc being relatively larger than the first fan-beam arc;
a first X-ray detector, to detect the first fan beam emitted by the first X-ray source;
a second X-ray detector, to detect the second fan beam emitted by the second X-ray source;
the filter arrangement of claim 3.

21. A computed tomography system, comprising:
a first X-ray source with a first X-ray energy level, to emit a first fan beam with a first fan-beam arc;
a second X-ray source with a second X-ray energy level, to emit a second fan beam with a second fan-beam arc, the second fan-beam arc being relatively larger than the first fan-beam arc;
a first X-ray detector, to detect the first fan beam emitted by the first X-ray source;
a second X-ray detector, to detect the second fan beam emitted by the second X-ray source;
the filter arrangement of claim 5.

22. The computed tomography system of claim 9, wherein when viewed in the fan-beam direction, the second X-ray detector includes outer detector regions which correspond to the outer filter regions of the filter arrangement and are set up to detect X-rays having a differing energy level which have been generated as a result of a differential X-ray beam hardening by the differing spectral filter functions of the first subregion and of the second subregion of the outer filter region.

23. The computed tomography system of claim 10, wherein when viewed in the fan-beam direction, the second X-ray detector includes outer detector regions which correspond to the outer filter regions of the filter arrangement and are set up to detect X-rays having a differing energy level which have been generated as a result of a differential X-ray beam hardening by the differing spectral filter functions of the first subregion and of the second subregion of the outer filter region.

24. The computed tomography system of claim 23, further comprising a reconstruction facility, set up to use the X-ray radiation acquired in the outer detector regions using differing energy levels for the reconstruction of image data separately according to the differing energy levels of the X-ray radiation.

25. The filter arrangement of claim 1, wherein the inner and outer filter regions of the filter arrangement are configured to pass and relatively increase spectral separation of the fan beam of the second X-ray source based upon the first, second and third spectral functions.

26. The computed tomography system of claim 9, wherein the inner and outer filter regions of the filter arrangement are configured to pass and relatively increase spectral separation of the fan beam of the second X-ray source based upon the first, second and third spectral functions.

27. The computed tomography system of claim 20, wherein the inner and outer filter regions of the filter arrangement are configured to pass and relatively increase spectral separation of the fan beam of the second X-ray source based upon the first, second and third spectral functions.

28. The computed tomography system of claim 21, wherein the inner and outer filter regions of the filter arrangement are configured to pass and relatively increase spectral separation of the fan beam of the second X-ray source based upon the first, second and third spectral functions.

* * * * *